(12) United States Patent
Attardo et al.

(10) Patent No.: US 8,707,598 B2
(45) Date of Patent: Apr. 29, 2014

(54) DOUBLE UMBILICAL IDENTIFICATION DEVICE MOTHER-INFANT, AND METHOD THEREOF

(76) Inventors: Giuseppe Attardo, Palermo (IT); Giada Maria La Scalia, Agrigento (IT)

( * ) Notice: Subject to any disclaimer, the term of this patent is extended or adjusted under 35 U.S.C. 154(b) by 0 days.

(21) Appl. No.: 13/810,070

(22) PCT Filed: Jul. 20, 2011

(86) PCT No.: PCT/IT2011/000255
§ 371 (c)(1),
(2), (4) Date: Jan. 14, 2013

(87) PCT Pub. No.: WO2012/011140
PCT Pub. Date: Jan. 26, 2012

(65) Prior Publication Data
US 2013/0111792 A1    May 9, 2013

(30) Foreign Application Priority Data
Jul. 22, 2010    (IT) ............................... PA2010A0028

(51) Int. Cl.
*G09F 3/00*    (2006.01)
*A61B 17/42*   (2006.01)

(52) U.S. Cl.
CPC .............. *A61B 17/42* (2013.01); *G09F 3/005* (2013.01)
USPC .......................................... 40/633; 606/120

(58) Field of Classification Search
USPC ............................ 40/633; 606/120, 157–158
See application file for complete search history.

(56) References Cited

U.S. PATENT DOCUMENTS

| 5,006,830 | A  |   | 4/1991  | Merritt |
|-----------|----|---|---------|---------|
| 5,484,060 | A  | * | 1/1996  | Middle et al. ................. 206/438 |
| 5,608,382 | A  |   | 3/1997  | Webb et al. |
| 5,676,672 | A  |   | 10/1997 | Watson et al. |
| 5,771,664 | A  | * | 6/1998  | Recchia, Jr. .................... 53/417 |
| 5,778,574 | A  | * | 7/1998  | Reuben ...................... 40/124.03 |
| 6,212,808 | B1 | * | 4/2001  | Rubel ............................ 40/633 |
| 7,402,164 | B2 |   | 7/2008  | Watson, Jr. et al. |
| 2007/0219582 | A1 | * | 9/2007 | Brunelle et al. .............. 606/207 |

FOREIGN PATENT DOCUMENTS

WO    01/19247 A1    3/2001

OTHER PUBLICATIONS

International Search Report, dated Nov. 3, 2011, from corresponding PCT application.

* cited by examiner

*Primary Examiner* — Joanne Silbermann
*Assistant Examiner* — Christopher e Veraa
(74) *Attorney, Agent, or Firm* — Young & Thompson

(57) ABSTRACT

A double umbilical identification device mother-infant, includes: an identification armband (1) for the mother provided with irreversible closing element (4, 5) and with an identification code (8); a first umbilical clamp (2) and a second umbilical clamp (3) for the newborn, irreversibly marked with the same identification code (8) of the armband (1); wherein the armband (1) is connected to the clamps (2, 3) by connecting rings (6, 7) made out of easily removable plastic material, characterized in that the device includes a sterile bag (200) connected by a first ring (6) to the armband (1), the sterile bag (200) containing the first clamp (2), and a second sterile bag (300) being connected by a second ring (7) to the first clamp (2), the second sterile bag (300) containing the second clamp (3). A mother-infant identification method making use of a double umbilical device is also described.

10 Claims, 2 Drawing Sheets

DOUBLE UMBILICAL IDENTIFICATION DEVICE MOTHER-INFANT, AND METHOD THEREOF

The present invention relates to the medical field, and in particular to those codified systems which allow identification of the newborns at birth. The suggested system allows to univocally identify the newborn by using two umbilical clamps having the same identification code which is also reproduced on the mother's identification armband.

There are many proposals relating to mother-child codified identification systems.

The best known and most spread systems mainly consist in two identification armbands, one for the mother and one for the newborn respectively.

The guidelines on the identification procedure for the newborn at birth, published in the Official Gazette of the Italian Republic in the ordinary supplement No. 19 of 23 Jan. 2002, foster the adoption of identification systems providing the use of two codified armbands for mother and child, so as to avoid newborn exchanges.

The choice of using a system that, on the newborn's side, does not make use of an armband but of a codified clamp, firmly and inseparably applied to him/her from the first cut of the umbilical cord to at least his/her first five days of life, appears to be safer.

Two U.S. patents are known to the art (U.S. Pat. No. 5,484,060 and U.S. Pat. No. 5,608,382) in which said identification system suggests only one codified clamp that is to be applied only after the cut of the umbilical cord and after having brought the newborn on the neonatal microenvironment.

This system is suggested as an alternative to the armbands so as to prevent circulation damages to the newborn due to the constriction caused by the armband and/or for guaranteeing the sterility thereof. Above mentioned devices do not really guarantee the identification in a very critical phase for the exchange (when many babies are born at the same time) between the umbilical cord's cut in the delivery room and the transfer of the newborn on the cot of the neonatal microenvironment, used for the neonatal stabilization. In fact, the only available clamp may be applied only after the neonatal stabilization and after having dismissed the need of any resiscitative manoeuvre for which a long piece of umbilical cord is indispensible (>15 cm).

The present invention has the innovation, with respect to both mentioned patents, of comprising two clamps and not one, thus assuring the identification of the newborn during the whole after-birth period, "from the birth to the dismissal from the nursery".

U.S. Pat. No. 6,212,808 B1 describes a mother-child identification method making use of a double umbilical device according to the preamble of the main independent claim of the present invention, and said US patent comprises two clamps that must be contemporarily applied, at birth, respectively the first to the umbilical cord stump attached to the newborn and the second one to the umbilical cord stump that remains with the placenta, but it still provides the use of an armband for the newborn's identification during his/her stay in the nursery, when its umbilical cord stump has been cut and reduced to only a few centimeters of length and, with the portion of the cut cord, the relative clamp has gone, the risk of loosing the identification armband of the newborn during the normal cleaning, changing and feeding operations and during the paediatric checks being still high.

It is the aim of the present invention to provide a mother-child identification system at birth that overcomes all disadvantages of the known systems and increases the identification safety.

The present invention, therefore, consists of a system comprising a maternal armband and two umbilical clamps having the same numeric identification code of the maternal armband, and that provides the sterile packaging of each clamp and that ensures the subsequent availability and sterility of the packaging elements in which they are contained, thus determining a specific and intuitive progression in time of the operations to be performed using of the elements that make the system.

According to this realization scheme, the suggested invention is extremely easy and safe and may be easily used.

The aims set forth are reached by means of an identification armband and two identification umbilical clamps for the mother-child identification, according to the main independent claim.

Further features of the device according to the present invention are contained in the dependent claims.

The present invention also concerns a method for mother-child identification.

The device according to the present invention has strongly innovative and different features with respect to known identification systems, which bring along many advantages:

- due to the packaging of the components into sterile bags contained one in the other, the device according to the present invention allows to maintain the sterility of each component contained therein still after the application of the armband to the mother. This makes possible the use of sterile clamps in a sterile environment by mean of sterile operators;
- due to the use of two clamps, it assures a safer identification of the newborn throughout the post-natal period from the birth, along the hospitalization and until the dismissal from the nursery, thus avoiding possible exchanges of newborns;
- it allows a univocal and certain mother-child identification, codified by means of an alpha-numerical code both at birth in the delivery room and during the stay in the nursery: indeed as the combination newborn+clamp will be indivisible for at least five days from birth;
- it allows to avoid possible exchanges of newborn in the two most critical moments, the first one during delivery and the second one during the stay in the nursery;
- it allows to avoid the newborns exchange due to the second clamp that will be applied at a few centimeters on the umbilical cord projecting from the baby and that will remain there for at least five days, which is more than the three days a baby usually stays at the nursery;
- besides the mother-child identification method is very simple, easy to apply and assures a greater safety to the newborn.

The present invention will be explained more in detail, with reference to the drawings, which represent a non-limiting preferred embodiment, wherein.

Figure 1:
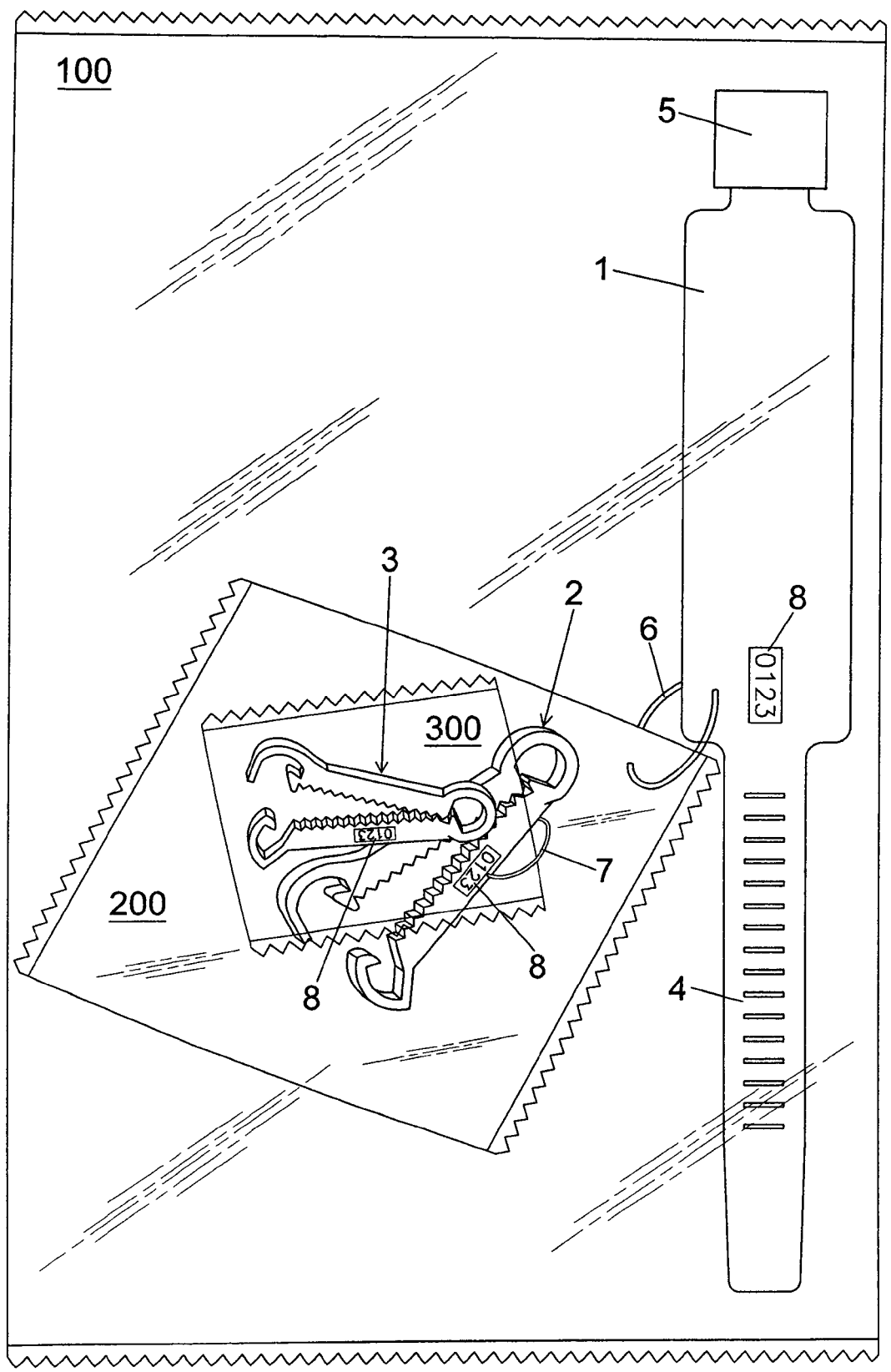
FIG. 1 shows a front view of the double umbilical mother-child identification device, according to the present invention.
Figure 2:
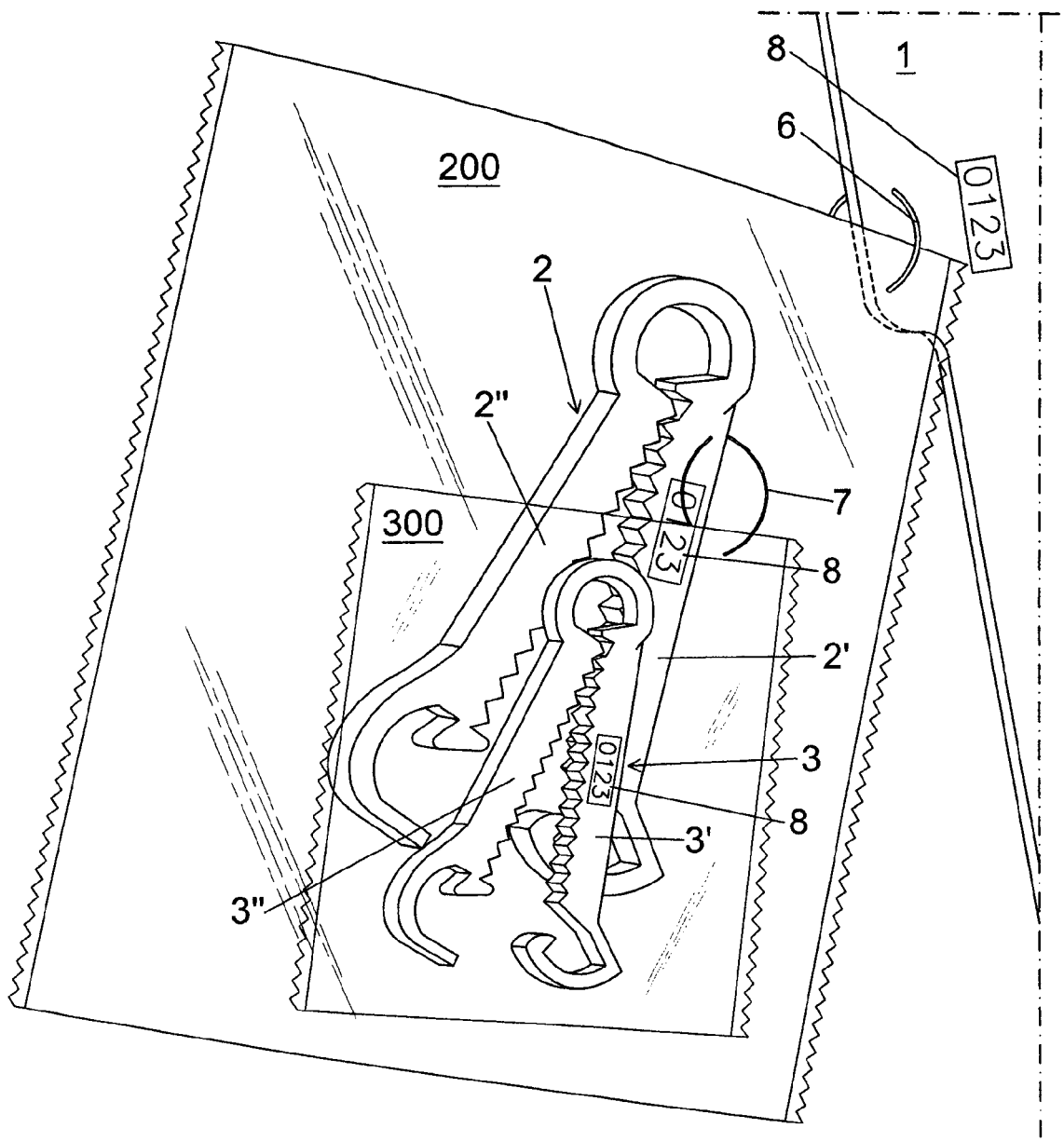
FIG. 2 shows a front view of a detail of the connection system between the components of the device according to the present invention.

With reference to the details shown in the figures, the double umbilical mother-child identification device mainly comprise three elements contained in one single sterile packaging:

an identification armband 1 for the mother, to be applied to the wrist or to the ankle;

a first clamp 2, to be applied at the cut of the umbilical cord after delivery, at about 50 cm to the portion of the cord projecting from the newborn;

a second clamp 3, to be applied in a second time, at about 5 cm to the umbilical cord projecting from the baby, when the length thereof is reduced on the neonatal cot.

All materials used for composing the system are light, hypoallergenic and sterile.

The packaging containing the three elements is arranged like the "nesting boxes" type system so as to assure the correct and unchangeable progression of the phases of the utilization process.

In detail, the device according to the present invention comprises a first sterile bag 100, containing both the armband 1 for the identification of the mother and a second sterile bag 200.

The second bag 200 in turn contains both the first clamp 2 and a third sterile bag 300.

The third bag 300 contains the second clamp 3.

The bags 100, 200 and 300 are made out of transparent, thin and soft plastic material.

The armband 1 for the identification of the mother is made out of flexible plastic material and is provided with an adjustable hermetic non-reopenable closure, comprising a toothed band 4 arranged for cooperating with an irreversible closing buckle 5.

The armband 1 comprises a ring 6 made out of thin plastic material, that may easily be broken and removed, to which a second bag 200 is applied and which therefore is easily detachable from said armband when it is needed, in order to use first clamp 2.

Clamp 2 comprises a ring 7 made out of thin plastic material, that may easily be broken and removed, to which the third bag 300 is applied, and which therefore is easily detachable from the clamp itself at a suitable time, in order to use second clamp 3.

The two clamps 2 and 3 are made out of stiff, sterile plastic material, provided with a hermetic non-reopenable closure, and comprise two arms 2', 2", 3' and 3", connected at one end by a hinge made out of easily deformable plastic material. The opposite end of the arms comprises shaped parts arranged for getting hooked one into the other in an irreversible way.

Said arms are toothed in the inwards facing part of the clamp, so as to easily grip the umbilical cord.

The shape of clamps 2 and 3 is substantially the same, but the dimensions are different. Indeed the first clamp 2 is one and a half times as long as the second clamp 3 and the respective lengths are of about 9 and 6 cm, so as to adapt to the different use conditions.

Both armband 1 and clamps 2 and 3 have the same numerical or alpha-numerical identification code 8 that identifies the device.

The code is not stamped with ink, but directly obtained by pressing of the plastic material so as to make it unmodifiable.

Furthermore, both armband 1 and the two clamps 2 and 3 have the same colour, for a more intuitive recognition of the components of the same packaging.

The packagings in fact may contain all white or yellow or green components and in this case, in particular, for every three progressive numbers of the code the same colours of the components will be used: white, yellow and green.

Due to the respective connections obtained by means of rings 6 and 7, a sterilized bag 200 containing the bigger clamp 2 is directly connected to armband 1 for the identification of the mother, and to said armband a sterilized second bag 300 is indirectly connected, in turn containing the second smaller clamp 3. Both clamps 2 and 3 are to be applied to the umbilical cord of the newborn and are irreversibly associated to it, even if in different periods of the life of the newborn.

The utilization process of the double umbilical identification device mother-infant will be described hereinbelow.

The non-reopenable umbilical clamps 2, 3 have the same progressive identification numerical code 8 as the recognition armband of the mother, which too is non-reopenable, and that will be hermetically applied to the arm or to the ankle of the mother before birth.

Both clamps 2 and 3 are to be applied to the umbilical cord of the newborn, but in different moments.

The first umbilical clamp 2 is applied to the umbilical cord before cutting the funiculus, straight after the expulsion of the newborn, at about 50 cm from the baby, and will be removed after birth on the neonatal stabilization cot (always after the application of the second clamp 3), by simply cutting the exceeding part of the umbilical cord, thus leaving the second clamp 3 connected to the baby (at about 5 cm on the umbilical cord projecting from the baby).

The second umbilical clamp 3 may be removed from the newborn only at his/her dismissal from the nursery, or later, braking it with an appropriate nipper, or it will fall away together with the umbilical cord stump between the $5^{th}$ and the $11^{th}$ day of the baby's life, due to the natural mummification process.

The device according to the present invention will assure a univocal and certain codified mother-child identification both at birth in the delivery room and during the baby's stay in the nursery; the combination newborn+clamp, in fact, will be indivisible for at least five days from birth.

The use of two clamps means to increase the safety of the device, so as to avoid exchanges mainly in the delivery room and in the nursery.

The exchange risk in fact has two critical moments: the delivery room and the stay in the nursery.

The delivery room is at risk for what concerns the newborns exchange because of the possibility of contemporary deliveries, which is not a rare event.

In order to avoid babies' exchanges at birth, before the cut of the umbilical cord that separates the mother from the newborn, the first numbered clamp 2 is applied for assuring the identification mother-infant since the first cut of the umbilical cord.

The first clamp 2 will remain with the newborn after the cut of the umbilical cord and during transportation from the delivery room to the neonatal positioning cot for the neonatal stabilization.

The first codified clamp 2 will be applied at about 50 cm from the newborn for allowing possible resuscitation manoeuvres like drug infusions, catheterisms or other which all need a long portion of umbilical cord (>15 cm).

The first clamp 2 must be removed from the newborn after birth, on the neonatal positioning cot (always after the second clamp 3 has been applied), by simply cutting the exceeding part of the umbilical cord, after having checked there is no need of resuscitation. The second codified clamp 3 (applied at 3-5 cm to the umbilical cord projecting from the newborn) will remain with the newborn for as long as he/she stays in the nursery.

The stay in the nursery is a second critical moment, in particular when the babies are gathered all in one single room and undressed for cleaning and medical check ups: it is not unusual to find babies without neonatal identification armband, which may have slipped from the wrist or from the ankle (>5%).

This may give origin to the legitimate protests of the parents as well as to newborn exchange.

The application of the second codified clamp 3 solves also this problem as it is inseparable from the newborn for at least five days (the stay in the nursery does not exceed three days).

For an easier identification of the two clamps, the first is 9 cm long, i.e. one and a half times as long as the second one, which is about 6 cm. Besides, the bigger dimensions of the first clamp are meant for easing the complicated clamping operations during delivery.

The aim reached by means of the device according to the present invention is to have an identification device and system easy to be applied and of greater safety for the newborn.

The invention claimed is:

1. A double umbilical identification device mother-infant, comprising:
    an identification armband (1) for the mother provided with irreversible closing means (4, 5) and with an identification code (8);
    a first umbilical clamp (2) and a second umbilical clamp (3) for the newborn, irreversibly marked with the same identification code (8) of the armband (1);
    wherein said armband (1) is connected to said clamps (2, 3) by means of connecting rings (6, 7) made out of easily removable plastic material,
    characterized in that said device comprises a sterile bag (200) connected by a first ring (6) to said armband (1), said sterile bag (200) containing said first clamp (2), and a second sterile bag (300) being connected by a second ring (7) to said first clamp (2), said second sterile bag (300) containing said second clamp (3).

2. A double umbilical identification device mother-infant according to claim 1, characterized in that said identification code (8) is a numerical or alpha-numerical code.

3. A double umbilical identification device mother-infant according to claim 1, characterized in that it comprises a bag (100) arranged for containing said armband (1) and said bag (200).

4. A double umbilical identification device mother-infant according to claim 1, characterized in that said first and second clamps (2, 3) comprise means for an irreversible closure.

5. A double umbilical identification device mother-infant according to claim 1, characterized in that said first clamp (2) is one and a half times as long as said second clamp (3).

6. A double umbilical identification device mother-infant according to claim 5, characterized in that said first clamp (2) is 9 cm long and that said second clamp (3) is 6 cm long.

7. A double umbilical identification device mother-infant according to claim 1, characterized in that said armband (1) and said first and second clamps (2, 3) are of the same colour.

8. A double umbilical identification device mother-infant according to claim 7, characterized in that said colour varies according to the different numerical code (8) and is repeated in sequence.

9. A sterile packaging characterized in that it contains a double umbilical identification device mother-infant according to claim 1.

10. A method for mother-child identification, comprising the following phases:
    to provide a double umbilical identification device mother-infant according to claim 1;
    to apply an armband (1) to a limb of the mother;
    to apply a first clamp (2) to the umbilical cord projecting from the newborn straight after birth at a distance of 50 cm;
    to cut the umbilical cord separating the mother from the child, leaving said clamp (2) applied to the baby's umbilical cord;
    to apply a second clamp (3) to the umbilical cord projecting from the newborn when he/she is on the neonatal positioning cot, at a distance of 5 cm from the newborn;
    to cut the portion of the umbilical cord exceeding 5 cm together with first clamp (2) applied thereto.

* * * * *